(12) United States Patent
Steenkamp

(10) Patent No.: US 7,619,121 B2
(45) Date of Patent: Nov. 17, 2009

(54) METHOD FOR ISOLATING A THIOL

(75) Inventor: Daniel Jacobus Steenkamp, Houtbay (ZA)

(73) Assignee: University of Cape Town, Cape Town (ZA)

( * ) Notice: Subject to any disclaimer, the term of this patent is extended or adjusted under 35 U.S.C. 154(b) by 0 days.

(21) Appl. No.: 10/569,710

(22) PCT Filed: Aug. 27, 2004

(86) PCT No.: PCT/IB2004/002774

§ 371 (c)(1),
(2), (4) Date: Mar. 8, 2007

(87) PCT Pub. No.: WO2005/021493

PCT Pub. Date: Mar. 10, 2005

(65) Prior Publication Data

US 2007/0232836 A1    Oct. 4, 2007

(30) Foreign Application Priority Data

Aug. 27, 2003  (ZA) ................................. 2003/6684

(51) Int. Cl.
*C07C 319/00* (2006.01)
(52) U.S. Cl. ....................................................... 568/61
(58) Field of Classification Search ................... 568/21, 568/18, 61; 530/336
See application file for complete search history.

(56) References Cited

U.S. PATENT DOCUMENTS 2,820,780 A * 1/1958 Gutcho et al. ............... 530/336
6,780,418 B1 * 8/2004 Fahey et al. .............. 424/248.1

FOREIGN PATENT DOCUMENTS

WO    WO 99/21580 A1    5/1999

OTHER PUBLICATIONS

Gharbia et al., Isolation Purification and Characterization of 2 Oxoglutarate Reductase From Fusobacterium-Nucleatum. Gharbia et a.,FEMS Microbiology Letters, (1991) vol. 80, No. 2-3, pp. 283-288, Abstract.*
Landino et al., Redox modulation of tau and microtubule-associated protein-2 by the glutathione/glutaredoxin reductase system; Biochem. Biophys. Res. Commun. 2004, vol. 323, No. 1, pp. 112-117.*
Chassaing et al., Determination of reduced and oxidized homocysteine and related thiols in plasma by thiol-specific pre-column derivatization and capillary electrophoresis with laser-induced fluorescence detection, Journal of chromatography. B, Biomedical sciences and applications, (1999), 735(2), 219-227, Abstract.*
Gundermann, K. D., et al. Methoden Der Organischen Chemie (Houben-Weyl) Band E11, 1985, Georg Thieme Verlag, Stuttgart, New York, XP002316126, pp. 48, 140-143.
Spies, H. S. C., et al. Thiols of Intracellular pathogens: Identification of Ovothiol a in Leishmania Donovani and Structural Analysis of a Novel Thiol from Mycobacterium Bovis (BCG), Eur. J. Biochem., vol. 224, 1994, pp. 203-213, XP000673267, Figs. 1-4.

* cited by examiner

*Primary Examiner*—Sikarl A. Witherspoon
*Assistant Examiner*—Chukwuma O Nwaonicha
(74) *Attorney, Agent, or Firm*—Fitch, Even, Tabin & Flannery

(57) ABSTRACT

A method of detecting a member of the taxa actinomycetes is provided. A method also is provided for detecting mycothiol or precursor thereof. An antibody is provided when binds to mycothiol or a mycothiol precursor. A method is further provided for diagnosis of a subject having or at risk of having an actinomycetes-associated disorder. A method is also provided for identifying a sample with altered production of mycothiol or a precursor thereof. A method is provided for detecting mycothiol or precursor thereof in a bacterial colony. Kits are also disclosed which are useful for detecting the presence of mycothiol or precursor thereof in a sample.

7 Claims, 5 Drawing Sheets ated in the detoxification of noxious chemicals, such as are produced in macrophage respiratory burst and in the more prolonged release of nitric oxide by activated macrophages (Nathan C. and Shiloh M U (2000) Reactive oxygen and nitrogen intermediates in the relationship between mammalian hosts and microbial pathogens. *Proc. Natl. Acad. Sci USA.* 97, 8841-8). They also play a role (i) in the sequestration of alkylating agents and their conversion to mercapturic acids, which are excreted (Fahey R C (2001) Novel thiols of prokaryotes. *Annu Rev Microbiol.* 55, 33-356; Newton G L, Av-Gay Y and Fahey R C (2000) A novel mycothiol dependent detoxification pathway in mycobacteria involving mycothiol S-conjugate amidase. *Biochemistry* 39, 10739-46), (ii) in providing reducing equivalents for ribonucleotide reductase, a key enzyme in DNA synthesis and consequently cell division (Dormeyer M, Reckenfelderbaumer N, Ludemann H, and Krauth-Siegel R L (2001) Trypanothione-dependent synthesis of deoxyribonucleotides by *Trypanosoma brucei* ribonucleotide reductase. *J. Biol. Chem.* 276, 10602-6; Aslund F, Ehn B, Miranda-Vizuete A, Pueyo C, Holmgren A. (1994) Two additional glutaredoxins exist in *Escherichia coli*: glutaredoxin is a hydrogen donor for ribonucleotide reductase in a thioredoxin/glutaredoxin 1 double mutant *Proc Natl Acad Sci USA* 91, 9813-7), and (iii) in the redox regulation of metabolism by modulating the activity of enzymes involved in signalling cascades (Sen C K (2000) Cellular thiols and redox regulated signal transduction. *Curr. Top. Cell Regul.* 36, 1-30; Schafer F Q and Buettner G R (2001) Redox environment of the cell as viewed through the redox state of the glutathione disulphide/glutathione redox couple. *Free Radical Biology & Medicine* 30, 1191-1212).

Trypanosomatids do produce glutathione, as do most eukaryotes and gram negative bacteria capable of aerobic growth, but then conjugate it to spermidine to form $N^1,N^8$-(bis-glutathionyl)-spermidine (or trypanothione), a metabolite thought to only occur in the Kinetoplastida (Fairlamb A H, Blackburn P, Ulrich P, Chait B T and Cerami A. (1985) Trypanothione: a novel bis(glutathionyl) spermidine cofactor for glutathione reductase in trypanosomatids. *Science* 227, 1485-1487; Fairlamb A H and Cerami A (1992) Metabolism and functions of trypanothione in the Kinetoplastida. *Ann. Rev Microbiol.* 46, 695-729).

Novel thiols have been identified in the Actinomycetes order of bacteria, including in the medically important *Mycobacterium tuberculosis*, the causative agent of tuberculosis, which produces 1-D-myo-inosityl-2-deoxy-2-(N-acetyl-L-cysteinyl)amino-α-D-glucopyranoside (or mycothiol) as principal thiol antioxidant (Spies H S C and Steenkamp D J (1994) Thiols of intracellular pathogens: Identification of ovothiol A in *Leishmania donovani* and structural analysis of a novel thiol from *Mycobacterium bovis* (BCG). *Eur. J. Biochem.* 224, 203-213; Fahey R C (2001) Novel thiols of prokaryotes. *Annu Rev Microbiol.* 55, 33-356), and in trypanosomatids which cause a wide spectrum of maladies, ranging from South American Chagas' disease to the various forms of New World and Old World leishmaniases. Trypanothione reductase, a member of the disulphide reductase family of enzymes, proved to be essential for the survival of trypanosomatids within the host (Grieger S, Schwarz W, Ariyanayagam M R, Fairlamb A H, Krauth-Siegel R L and Clayton, C. (2000) Trypanosomes lacking trypanothione reductase are avirulent and show increased sensitivity to oxidative stress. *Mol Microbiol* 35, 542-52; Tovar J, Wilkinson S, Mottram J C, Fairlamb A H (1998) Evidence that trypanothione reductase is an essential enzyme in *Leishmania* by targeted replacement of the tryA gene locus. *Mol. Microbiol* 29, 653-60; Dumas C, Quellette M, Tovar J, Fairlamb A H, Tamar S, Olivier M and Papadopoulou B. Disruption of the trypanothione reductase gene of *Leishmania* decreases its ability to survive oxidative stress in macrophages. *EMBO J.* 16, 2590-8). In recent work the probability of transposon mediated insertional inactivation of the genes of *M. tuberculosis* was determined by high density mutagenesis, in order to establish which genes were likely to be essential for growth in culture. This study predicted that both the third enzyme of mycothiol biosynthesis, mshC, and mycothioldisulphide reductase would be required for growth (Sassetti C M, Boyd D H, Rubin E J. (2003) Genes required for mycobacterial growth defined by high density mutagenesis. *Mol Microbiol.* 48, 77-84). Attempts to disrupt the mshC gene by allelic exchange yielded no viable progeny and also supported the indications that mycothiol is an essential metabolite in *M. tuberculosis* (Sareen D, Newton G L, Fahey R C, Buchmeier N A. (2003) Mycothiol is essential for growth of *Mycobacterium tuberculosis* Erdman. *J. Bacteriol.* 185, 6736-40).

Procedures for the diagnosis of tuberculosis, based on the immunochemical detection of mycothiol, are known but research in this area is hampered by the lack of availability of mycothiol. Mycothiol and ovothiol A, a mercaptohistidine which has been identified in trypanosomatids, are, for example, not available from commercial sources.

Chemical synthesis of the principal low molecular mass thiol from the mycobacteria, viz. mycothiol, has proven to be difficult and costly, and only small amounts of the compound could be isolated from natural sources, ie. the mycobacteria (Spies H S C and Steenkamp D J (1994) Thiols of intracellular pathogens: Identification of ovothiol A in *Leishmania donovani* and structural analysis of a novel thiol from *Mycobacterium bovis* (BCG). *Eur. J. Biochem.* 224, 203-213). The purification of thiol compounds from natural sources is complicated by their reactivity. Following their extraction thiols are readily oxidized to symmetrical and mixed disulphides. Thiols are especially unstable in mixtures where they are not only subject to atmospheric oxidation but also undergo addition reactions to electrophiles, such as aldehydes and activated double bonds. It is thus important to separate the thiol species from contaminants as soon as possible after extraction, or to convert them, in a manner that can readily be reversed, to a more stable form, such as the disulphide. It is an object of the invention to address this problem.

Accordingly the invention provides a method of isolating a thiol R'SH from a thiol-containing mixture, the method including the steps of forming a mixed disulphide R'SSR of the thiol R'SH in the mixture, in which R is a non-immobilised hydrophobic moiety;

purifying the mixed disulphide R'SSR;

reducing the purified mixed disulphide R'SSR to produce a mixture of the thiols R'SH and R'SH; and isolating the thiol R'SH.

Purifying the mixed disulphide R'SSR may include exploiting an increased hydrophobicity thereof relative to the thiol R'SH. More particularly, the mixed disulphide R'SSR may be purified by chromatography. Instead, the mixed disulphide R'SSR may be purified by selective precipitation.

The mixed disulphide may be purified by means of reversed phase high performance liquid chromatography (HPLC).

Forming the mixed disulphide may include reacting the free thiol species R'SH with a mixed disulphide compound R"SSR, in which R" is a 2-thiopyridyl group and R is a non-polar thiol group.

The purified disulphide may be reduced with dithiothreitol or -mercaptoethanol.

The thiol R'SH may be isolated by high performance liquid chromatography (HPLC).

The HPLC may be performed on a C18 reversed phase medium having a polar mobile phase, such as, for example, water and/or acetonitrile.

The group R may be a substituted or unsubstituted polynuclear aromatic group. In particular, it may be a 6-hydroxynaphthyl group. The mixed disulphide may thus be 2-thiopyridyl-6-hydroxynaphthyldisulphide.

The thiol R'SH may be 1-D-myo-inosityl-2-deoxy-2-(N-acetyl-L-cysteinyl)amino-α-D-glucopyranoside, or mycothiol. This thiol is produced by the bacterium *Mycobacterium tuberculosis*. The disulphide may accordingly be 2-S-(mycothiolyl)-6-hydroxynaphthalenedisulphide.

According to another aspect of the invention, there is provided a disulphide of the formula R'SSR in which R'S is mycothiolyl and R of the substituent -RS is a hydrophobic moiety.

R may be a polynuclear aromatic group. It may, in particular, be the 6-hydroxynaphthyl group.

The invention will now be described, by way of example, with reference to the accompanying non-limiting examples and diagrammatic drawings.

Figure 3:
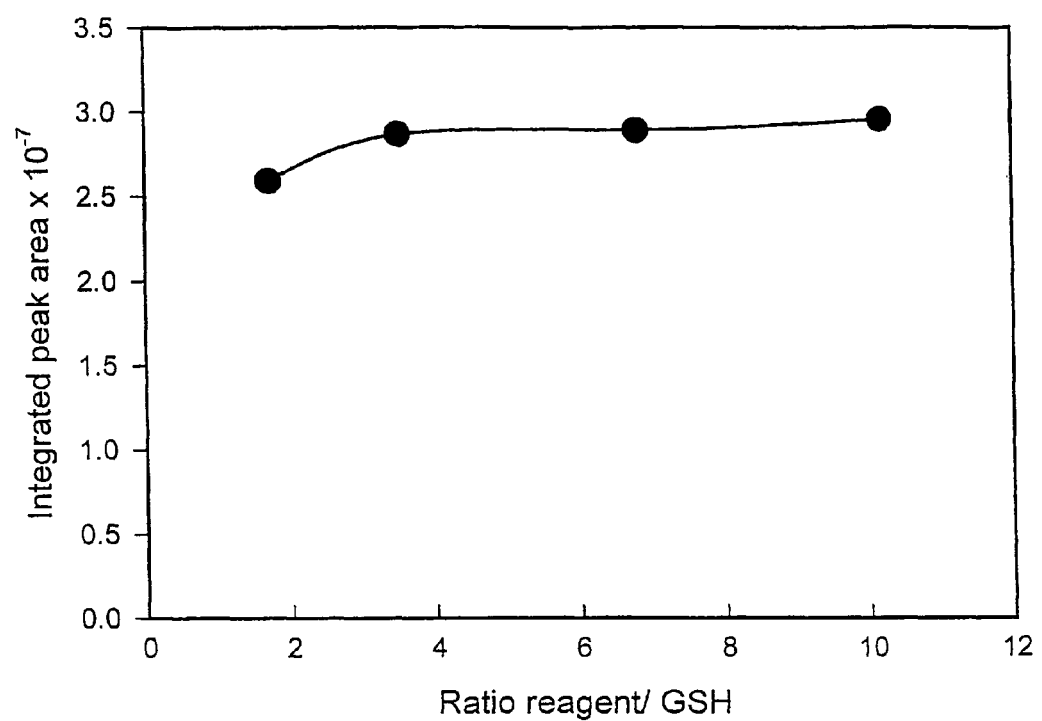
Figure 4:
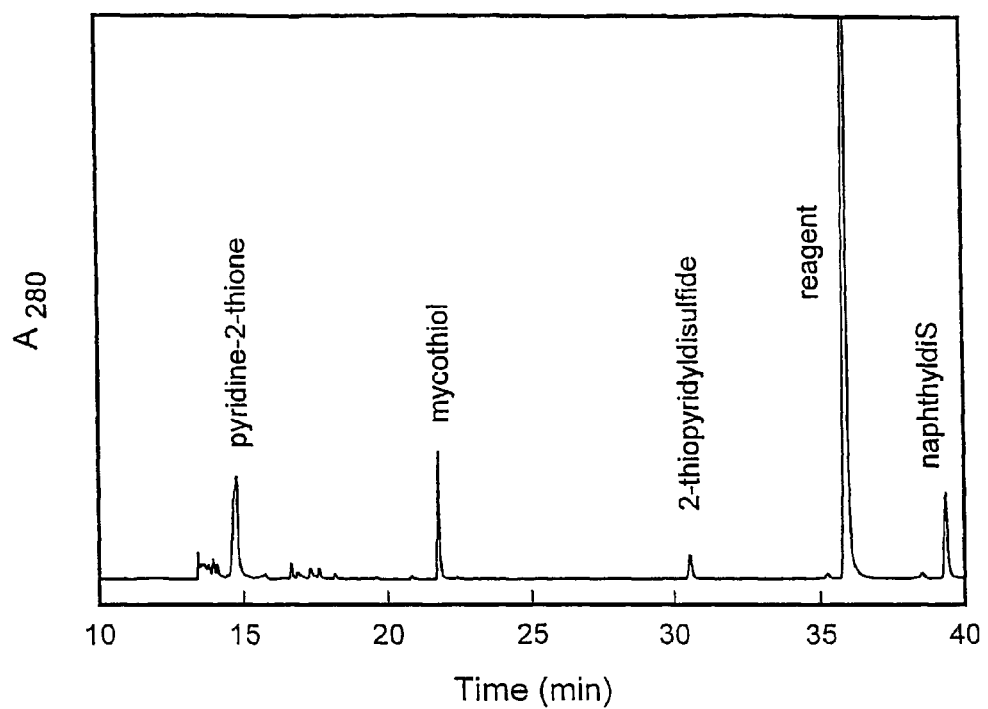
Figure 5:
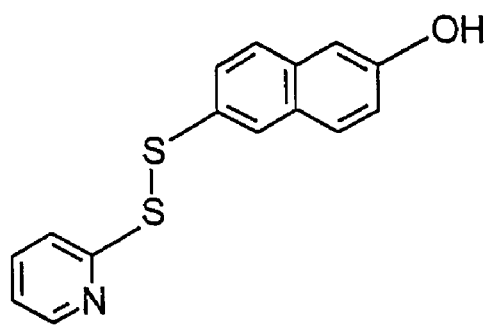
Figure 6:
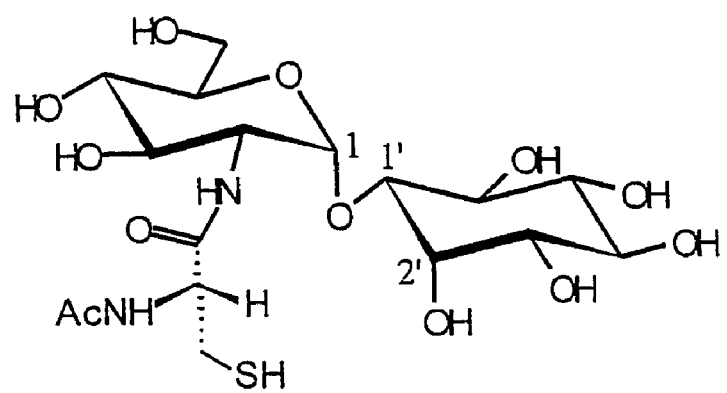

FIG. 3 shows the dependence of the recovery of glutathione as 2-S-(glutathionyl)-6-hydroxynaphthalene on the ratio of glutathione to 2-S-(2'-thiopyridyl)-6-hydroxynaphthalene (reagent). 100 l of 0.66 mM glutathione in a mixture containing 4 parts acetonitrile and 6 parts of 0.1M sodium acetate, pH 4.8, was mixed with different amounts of 2-S-(2'-thiopyridyl)-6-hydroxynaphthyldisulphide and incubated overnight at room temperature. The mixtures were then all adjusted to a volume of 0.5 ml. Aliquots were diluted with one part of water and injected onto a Phenomenex C18 reversed phase column (250×4.6 mm);

FIG. 4 shows an analytical HPLC of a perchloric acid extract of *Mycobacterium smegmatis* after treatment with 2-S-(2'-thiopyridyl)-6-hydroxynaphthyldisulphide for 100 min. Mycothiol; 2-S-(mycothiolyl)-6-hydroxynaphthyldisulphide, reagent; 2-S-(2'-thiopyridyl)-6-hydroxynaphthyldisulphide, naphthyldiS; 6-hydroxy-2-naphthyl-disulphide;

FIG. 5 shows the structure of 2-S-(2'-thiopyridyl)-6-hydroxynaphthyldisulphide; and FIG. 6 shows the structure of Mycothiol.

EXAMPLE 1

Synthesis of 2-S-(2'-thiopyridyl)-6-hydroxynaphthyldisulphide 100 mg 6-hydroxy-2-naphthyldisulphide (obtained from Sigma-Aldrich S.A.) was dissolved in 50 ml of a 1:1 mixture of acetonitrile and water and was reduced by the addition of 300 mg sodium borohydride at room temperature. Reduction resulted in the appearance of a yellow colour due to the formation of the thiolate anion of 2-thio-6-hydroxynaphthalene. (The molar extinction coefficient, $\epsilon_{298}$ was estimated to be 18.5 $mM^{-1}$ $cm^{-1}$ by recording the absorbance spectrum of an aliquot in 25 mM $K_2HPO_4$). The borohydride was destroyed by the addition of 1 ml glacial acetic acid and the pH of the resulting solution was adjusted to 4.6 by the addition of dipotassium phosphate. (The pH of 4.6 was chosen to be significantly below the $pK_a$ of 2-thio-6-hydroxynaphthalene, which was estimated to be approximately 6.4 by spectrophotometric titration.) The 2-thio-6-hydroxynaphthalene solution was then added dropwise and with stirring over a period of 20 minutes to 25 ml of a solution containing 237 mg 2,2'-dithiodipyridyl (obtained from Sigma-Aldrich S.A.) of the same solvent (i.e. 1:1 mixture of acetonitrile and water). The mixture was left for 20 minutes and was then diluted with one part of water and cooled to 4° C. The resultant precipitate was collected by centrifugation and was dissolved in a 50% acetonitrile/water mixture.

The precipitate consisted principally of 6-hydroxy-2-naphthyldisulphide and 2-S-(2'-thiopyridyl)-6-hydroxynaphthyldisulphide (for structure thereof, see FIG. 5). These components were separated on a Preparative Vydac TP1022 reversed phase HPLC column using a linear gradient over 40 minutes from 50% B to 100% B (A: 0.1% trifluoroacetic acid; B: 100% acetonitrile). It will be appreciated that the starting material, 6-hydroxy-2-naphthyldisulphide, obtained from this step can be recycled.

EXAMPLE 2

Use of 2-S-(2'-thiopyridyl)-6-hydroxynaphthyldisulphide

*Mycobacterium smegmatis* was cultured and was harvested in the late log phase of growth. 4 g (wet weight) of packed cells were suspended in 8 ml of a solution containing 2 mM EDTA and 0.75 M perchloric acid in a 1:1 mixture of acetonitrile and water. The cells were disrupted by sonication and the mixture clarified by centrifugation. The pH of the clear supernatant was adjusted to 4.8 by the addition of solid potassium carbonate and the potassium perchlorate precipitate was removed by centrifugation. The resulting mycobacterial extract contained 8 mole of dithiopyridyl reactive material in a volume of 9.3 ml. Mycothiol was purified from this extract by the following steps.

Step 1: Acetonitrile (6.2 ml) was added to the mycobacterial extract. A slight precipitate developed which was again clarified by centrifugation. The mycobacterial extract was subsequently added dropwise with stirring to 3.65 ml of a 60% v/v acetonitrile solution containing 16 moles of 2-S-(2'-thiopyridyl)-6-hydroxynaphtyldisulphide. Formation of 2-S-(mycothiolyl)-6-hydroxynaphthalenedisulphide was monitored by HPLC analysis of aliquots of the reaction mixture (see below under Analysis of reaction progress).

Step 2: After 3.5 hours the mixture was diluted five-fold with water and was then passed through a SepPak C18 cartridge. The cartridge washed with water. 2-S-(mycothiolyl)-6-hydroxynaphthyldisulphide was retained and could be eluted using a minimal quantity of 50% v/v acetonitrile/water. 2-S-(mycothiolyl)-6-hydroxynaphthyldisulphide can be detected in the effluent fractions by TLC (see below). By the SepPak step a large purification and concentration of the derivatized mycothiol is achieved.

Step 3: The acetonitrile content of the solution was subsequently reduced to less than 10% under a stream of nitrogen and the solution was chromatographed on a Preparative Vydac TP1022 C18 reversed phase column using the following conditions: 10 minutes at 100% A, followed by a gradient from 0-100% B over 40 minutes at a flow rate of 4 ml/min (A: 0.1% trifluoroacetic acid; B: acetonitrile). 2-S-(mycothiolyl)-6-hydroxynaphthalenedisulphide was eluted at 35.5 minutes as the principal component and only lesser contaminants were removed in this step. The concentration of 2-S-(mycothiolyl)-6-hydroxynaphthyldisulphide can be estimated by recording the absorbance spectrum of an aliquot in 25 mM $K_2HPO_4$ after reduction with 1 mM dithiothreitol and using $\epsilon_{298} = 18.5$ mM$^{-1}$ cm$^{-1}$. 1.43 moles of mycothiol was recovered as 2-S-(mycothiolyl)-6-hydroxynaphthyldisulphide.

Step 4: Reduced mycothiol (for structure thereof, see FIG. 6) was obtained by reduction of 2-S-(mycothiolyl)-6-hydroxynaphthyldisulphide with dithiothreitol and separation on the same preparative column, using the following conditions: 10 minutes at 100% A followed by a 40 minute gradient to 25% B (A: 0.1% trifluoroacetic acid; B: 100% acetonitrile) at a flow rate of 4.0 ml/min.

It will be appreciated that, when conducted on a larger scale, steps in which acetonitrile is removed under a stream of nitrogen can be replaced by vacuum distillation using a rotary evaporator.

Because of the large difference in polarity between mycothiol and mixed disulphides containing 2-thio-6-hydroxynaphthalene, considerable simplification of the above steps is possible. Instead of diluting the reaction mixture in Step 2, acetonitrile can be evaporated under a stream of nitrogen or by means of a rotary evaporator. This results in precipitation of 2-S-(2'-thiopyridyl)-6-hydroxynaphthalene disulphide and any 6-hydroxy-2-naphthyldisulphide which might have formed, while 2-S-(mycothiolyl)-6-hydroxynaphthyldisulphide remains in solution. Moreover, mycothiol can be obtained directly from the latter after Step 2, by reduction with 2-mercaptoethanol and extraction of the excess reductant with ethylacetate. Upon repeating the SepPak separation mycothiol will not be adsorbed, while 2-thio-6-hydroxynaphthalene and more apolar contaminants, which eluted from the SepPak cartridge in 50% acetonitrile, will selectively be retained.

Analysis of Reaction Progress:

The formation of the reagent 2-S-(2'-thiopyridyl)-6-hydroxynaphthyldisulphide and of 2-S-(mycothiolyl)-6-hydroxynaphthalenedisulphide was followed by HPLC on a 4.6×250 mm Phenomenex C18 reversed phase column using the same gradient conditions as for the chromatography of 2-S-(mycothiolyl)-6-hydroxynaphthalenedisulphide described above (ie. on the Vydac TP1022 column), but with a lower flow rate of 0.8 ml/min. The eluate was monitored at 280 nm and the concentrations of the components estimated from the integrated peak areas. In the case of 2-S-(mycothiolyl)-6-hydroxynaphthalenedisulphide the concentration of the compound in a solution, used to establish the necessary calibration curve, was determined with reference to the molar extinction coefficient of 2-thio-6-hydroxynaphthalene, which is liberated upon reduction, while pyridine-2-thione and 2-thio-6-hydroxynaphthalene served as standards for determination of the concentration of 2-S-(2'-thiopyridyl)-6-hydroxynaphthyldisulphide.

2-S-(2'-thiopyridyl)-6-hydroxynaphthyldisulphide and 6-hydroxynaphthyldisulphide were separated by TLC on silica gel G60 containing fluorescent indicator. The developing solvent was acetone: 0.1M Na-acetate: 4:6 (Rf values of 0.5 and 0.24, respectively). 2-S-(mycothiolyl)-6-hydroxynaphthalenedisulphide can be resolved from 2-S-(2'-thiopyridyl)-6-hydroxynaphthyldisulphide and 6-hydroxynaphthyldisulphide on cellulose containing fluorescent indicator using butanol:acetic acid:water (4:2:2) as developing solvent (Rf=0.7 for 2-S-(mycothiolyl)-6-hydroxynaphthalenedisulphide while 2-S-(2'-thiopyridyl)-6-hydroxynaphthyldisulphide and 6-hydroxynaphthyl-disulphide moved with the solvent front).

The fact that thiols form mixed disulphides with the thiopropyl group rather than with 2-thiopyridine, can be attributed to the favourable energy of ionization of 2-thiopyridine and the delocalization of charge on the thiolate anion into the pyridine ring. In the present invention, the thiol species to be isolated is reacted with a mixed disulphide between 2-thiopyridine and a non-polar thiol with significantly higher $pK_a$ of the thiol group than is the case for 2-thiopyridine. At a pH intermediate the $pK_a$ of the non-polar thiol and that of 2-thiopyridine the reaction of a thiol with the 2-thiopyridyl mixed disulphide is strongly biphasic, as follows:

$$2\text{-TP-SS-R} + \text{R'SH} \rightarrow 2\text{-TP-SH} + \text{RSSR'} \quad (1)$$

$$\text{RSSR'} + \text{R'SH} \leftrightarrow \text{R'SSR'} + \text{RSH} \quad (2)$$

In these reactions 2-TP represents 2-thiopyridyl, R is a non-polar thiol group and R'S a naturally occurring thiol species. The equilibrium in reaction (2) should preferably be far to the left.

Figure 2:
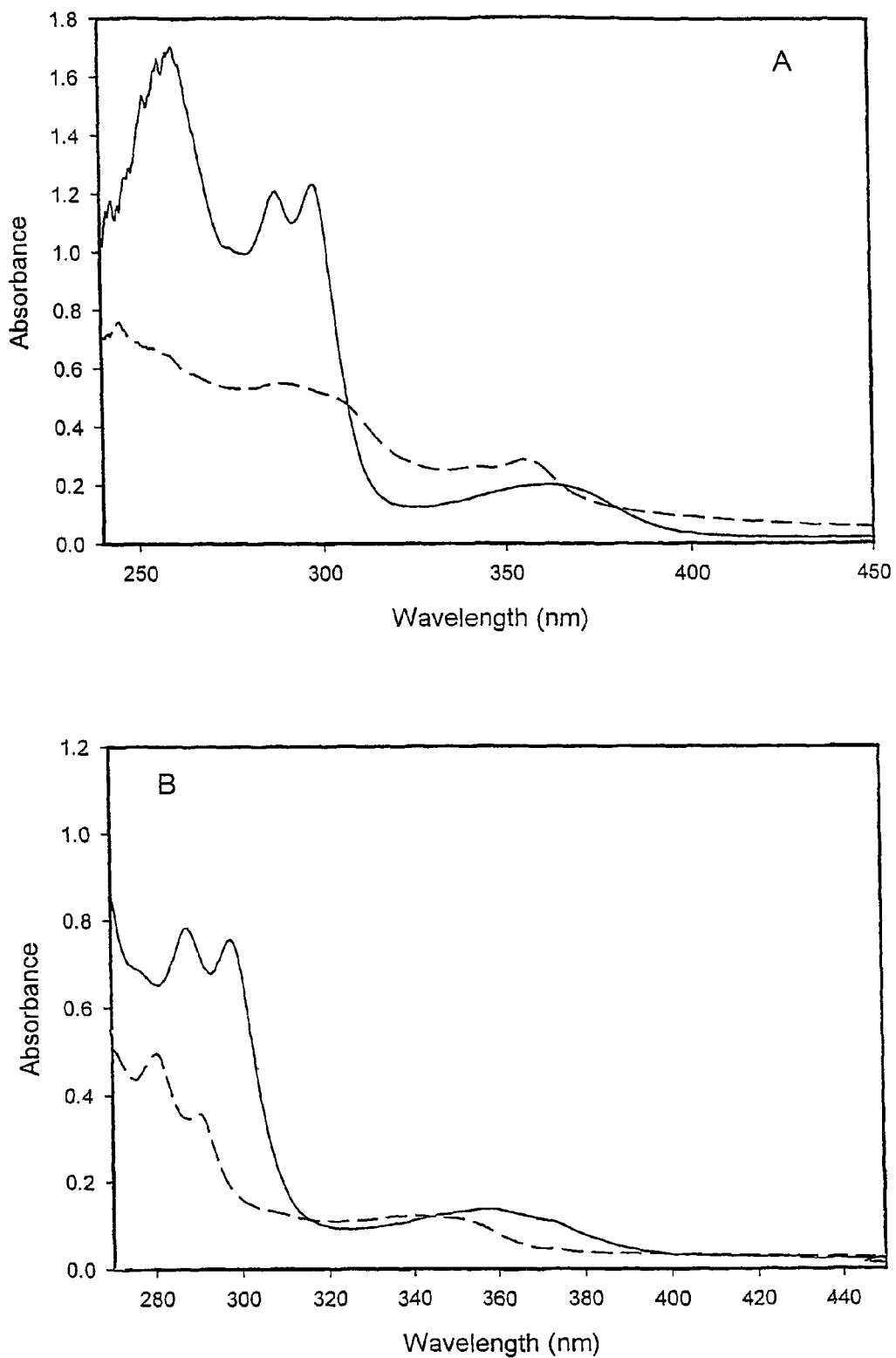
FIG. 2 shows absorbance spectra of (A) the 2-thio-6-hydroxynaphthalene thiolate anion (solid line) and of 6-hydroxy-2-naphthyldisulphide (broken line), (B) 2-thio-6-hydroxynaphthalene at pH 8.2 in 25 mM potassium phosphate buffer (solid line) and at pH 3.9 in 25 mM triethylammonium acetate (broken line)

In the above example it has been shown that 2-thio-6-hydroxynaphthalene satisfies the requirements for the non-polar thiol and generates a mixed disulphide, RSSR', which can be conveniently adsorbed and concentrated onto reversed phase materials. This greatly facilitates the isolation and purification of the compounds of interest, which can be recovered by reduction with an excess of dithiothreitol or -mercaptoethanol. Moreover, the thiolate anion of 2-thio-6-hydroxynaphthalene has characteristic absorbance bands which are convenient for the quantification of the amount of thiol with which it has associated to form a mixed disulphide (see FIG. 2).

Figure 1:
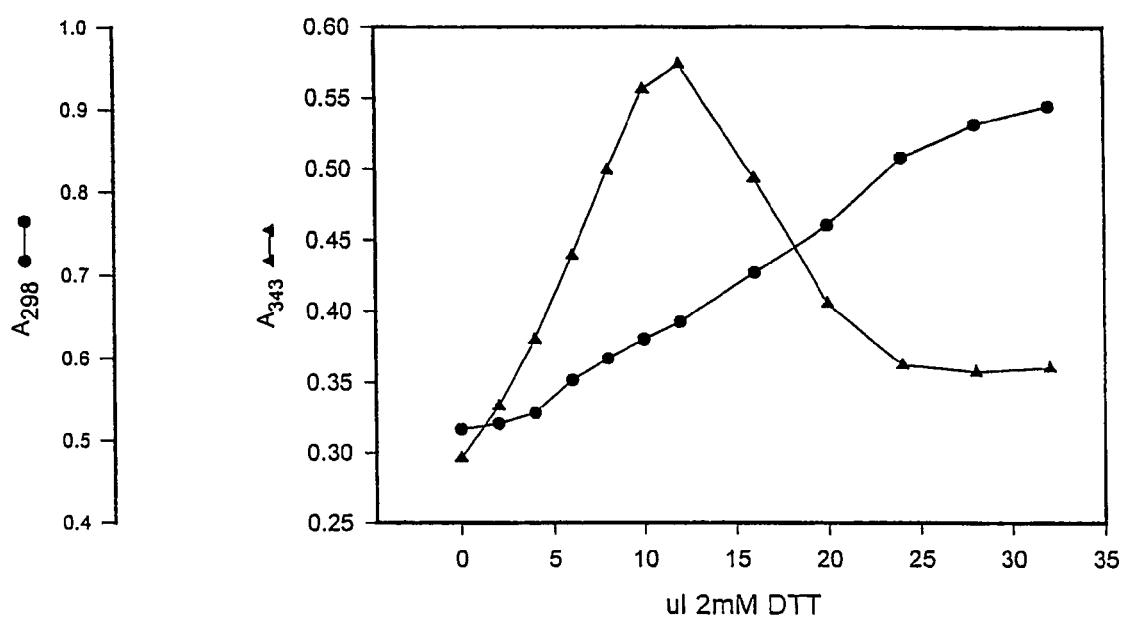
FIG. 1 shows the results of a spectrophotometric titration of 2-S-(2'-thiopyridyl)-6-hydroxynaphthyldisulphide in 25 mM triethylammonium-carbonate, pH 8.1, with dithiothreitol.

The reduction of 2-S-(2'-thiopyridyl)-6-hydroxynaphthyldisulphide by thiols, including dithiols such as dithiothreitol, proceeds in the biphasic manner set out above, with the initial release of pyridine-2-thione and the intermediate formation of a mixed disulphide of the reducing thiol with 2-thio-6-hydroxynaphthalene (see FIG. 1). In FIG. 1, the initial increase in absorbance at 343 nm can be attributed principally to the formation of pyridine-2-thione, while the subsequent decrease is due to the formation of the 2-thio-6-hydroxynaphthalene thiolate anion which has a lower absorbance as compared to the homo- and heterodisulphides at this wavelength (see FIG. 2A). With glutathione as the reducing thiol the formation of 2-S-(glutathionyl)-6-hydroxynaphthalenedisulphide is practically stoichiometric at pH values less than 5. The chromatographic behaviour of such mixed disulphides is governed to a large extent by the presence of the naphthol moiety. They are tightly bound on C18 reversed phase cartridges, but are eluted by water-miscible organic solvents. The amount of pyridine-2-thione released in the initial reaction can be quantified due to the absorbance of pyridine-2-thione at 343 nm ($\epsilon_{298}$=8.08 mM$^{-1}$ cm$^{-1}$) and the amount of mixed dithiol formed can be estimated from the intense absorbance of the thiolate anion (p$K_a$~6.5) of 2-thio-6 hydroxynaphthalene ($\epsilon_{298}$~18.5 mM$^{-1}$ cm$^{-1}$) which is formed when the mixed disulphide is reduced with dithiothreitol.

Spectra of oxidized and reduced 2-thio-6-hydroxynaphthalene are presented in FIG. 2A and in its protonated and thiolate forms in FIG. 2B.

In order to establish optimal conditions for the conversion of thiols to mixed disulphides by reaction with 2-S-(2'-thiopyridyl)-6-hydroxynaphthyldisulphide, glutathione was incubated overnight at room temperature with various amounts of the reagent. As shown in FIG. 3, the yield of 2-S-(glutathionyl)-6-hydroxynaphthalenedisulphide reaches a plateau at a ratio of about 3 moles of reagent per mole of glutathione. At a ratio of reagent to glutathione of 1.7, the conversion of glutathione to 2-S-(glutathionyl)-6-hydroxynaphthalenedisulphide reached a level of 72.7% after 100 minutes, showed a slight increase to 75.4% at 175 minutes and declined to 67.86% when the mixture was left overnight, presumably also because of thiol-disulphide equilibria which are established slowly between pyridine-2-thione and the mixed disulphides. This explanation was also supported by a significant increase in the integrated peak area for 6-hydroxy-2-naphthyldisulphide which is evidently a side product. At higher ratios of reagent to glutathione it is evident that a recovery of at least 75% of glutathione as 2-S-(glutathionyl)-6-hydroxynaphthalenedisulphide should be attainable.

The HPLC profile of a mixture which contained a perchlorate extract of *M. smegmatis* and 2-S-(2'-thiopyridyl)-6-hydroxynaphthyldisulphide 3.6-fold in excess of 4,4'-dithiodipyridyl reactive material is shown in FIG. 4. The reagent clearly has a high degree of specificity for thiols as evidenced by the prominence of the peak due to 2-S-(mycothiolyl)-6-hydroxynaphthyldisulphide at 21.9 minutes. The isolation of mixed disulphides containing the 2-thio-6-hydroxynaphthalene chromophore can be followed either by HPLC of aliquots or by TLC, in each case without any need for derivatization and the HPLC result can be used for quantification.

It is believed that the method described can be scaled up to allow for the purification of significant amounts of mycothiol. Approximately 600 g (wet weight) of *M. smegmatis* would be required for the isolation of 100 mg of mycothiol and extraction of this amount of cells with perchloric acid will generate 1.5 to 2 litres of extract. Converting the mycothiol in the extract to 2-S-(mycothiolyl)-6-hydroxynaphthyldisulphide, which can be selectively adsorbed and concentrated onto reversed phase material, would require only a three-fold excess of reagent over mycothiol and the success of the reaction can be directly evaluated by analytical HPLC as shown in FIG. 4.

The intermediates in the mycothiol biosynthetic pathway, such as, for example, 1-D-myo-inosityl-2-deoxy-2-amino-α-D-glucopyranoside (α-D-GI), are also not commercially available, but are accessible from mycothiol. *Mycobacteria* possess a deamidase which specifically cleaves alkylated mycothiol to α-D-GI and a mercapturic acid, which is excreted from the cells. The Applicant believes that α-D-GI could be a convenient starting point for the synthesis of inhibitors of the mycothiol biosynthetic pathway.

The invention provides an improved and more cost-effective method for the isolation and purification of low molecular mass thiols from natural sources. It is an advantage of the invention illustrated, that the mixed disulphide has a hydrophobic character which facilitates their isolation and purification. The compounds of interest can then be recovered by reduction with an excess of dithiothreitol or -mercaptoethanol. It is a further advantage that the method in accordance with the invention converts thiols to stable disulphides at an early stage in the isolation process and the greater part of purification is achieved in the first step of the method, which step can readily be scaled up. Furthermore, it dispenses with the need for the use of activated thiopropyl resins which are expensive to buy and which necessitate further purification steps to recover the thiols from the eluate of such columns.

The invention claimed is:

1. A method of isolating a thiol R'SH from a thiol-containing mixture, the method including the steps of
    forming a mixed disulphide R'SSR of the thiol R'SH by reacting the thiol R'SH with a second mixed disulphide R"SSR, in which R is a hydrophobic moiety which is not immobilised on a stationary phase, and R" is selected so that a forward reaction of the R'SH with the second mixed disulphide R"SSR to form R'SSR and R"SH is favoured over a reverse reaction of R"SH with R'SSR back to R"SSR and R'SH;
    purifying the mixed disulphide R'SSR by a process selected from selective precipitation and chromatography;
    reacting the purified mixed disulphide R'SSR with a reducing agent to produce the thiol-containing mixture of thiols R'SH and RSH; and
    separating the mixture of thiols R'SH and RSH to isolate the thiol R'SH, wherein R'SH is 1-D-myo-inosityl-2-deoxy-2-(N-acetyl-L-cysteinyl)amino-α-D-glucopyranoside or mycothiol, the second mixed disulphide R"SSR is 2-thiopyridyl-6-hydroxynaphthyldisulphide, and R" is a 2-thiopyridyl group.

2. The method as claimed in claim 1, wherein purifying the mixed disulphide R'SSR includes exploiting an increased hydrophobicity thereof relative to the thiol R'SH.

3. The method as claimed in claim 1, wherein the mixed disulphide is purified by means of reversed phase high performance liquid chromatography (HPLC).

4. The method as claimed in claim 1, wherein the reducing agent is selected from a group consisting of dithiothreitol and β-mercaptoethanol.

5. The method as claimed in claim 1, comprising separating the mixture of thiols R'SH and RSH by high performance liquid chromatography (HPLC).

6. The method as claimed in claim 5, wherein the high performance liquid chromatography is performed on a C18 reversed phase medium.

7. The method as claimed in claim 1, wherein the mixed disulphide R'SSR is 2-S-(mycothiolyl)-6-hydroxynaphthalenedisulphide.

* * * * *